(12) United States Patent
Webb

(10) Patent No.: US 6,745,763 B2
(45) Date of Patent: Jun. 8, 2004

(54) VAPORIZING DEVICE FOR ADMINISTERING STERILE MEDICATION

(76) Inventor: Garth T. Webb, 18040 - 20th Avenue, White Rock, British Columbia (CA), V4P 1M6

(*) Notice: Subject to any disclaimer, the term of this patent is extended or adjusted under 35 U.S.C. 154(b) by 0 days.

(21) Appl. No.: 09/250,272

(22) Filed: Feb. 16, 1999

(65) Prior Publication Data

US 2002/0195100 A1 Dec. 26, 2002

Related U.S. Application Data

(60) Provisional application No. 60/105,725, filed on Oct. 27, 1998.

(51) Int. Cl.[7] .................... A61M 15/00; A61M 16/10
(52) U.S. Cl. ............. 128/203.12; 222/96; 222/540; 137/843; 137/844; 137/850; 137/859
(58) Field of Search ............ 128/200.14, 203.12; 222/540, 541.1, 541.7, 541.8, 92, 95, 96, 105, 106, 107; 239/349, 357; 137/843, 844, 850, 859

(56) References Cited

U.S. PATENT DOCUMENTS

| | | | | |
|---|---|---|---|---|
| 395,436 A | * | 1/1889 | Green .................. 128/203.12 |
| 2,083,282 A | * | 6/1937 | Thompson ................. 239/359 |
| 2,213,846 A | * | 9/1940 | Meyer ...................... 239/359 |
| 2,510,712 A | * | 6/1950 | Olowinski ............. 128/203.12 |
| 2,918,221 A | * | 12/1959 | Viard ...................... 239/355 |
| 3,112,074 A | * | 11/1963 | Green ...................... 239/359 |
| 3,176,712 A | * | 4/1965 | Ramsden .................. 137/496 |
| 3,240,431 A | * | 3/1966 | Hug et al. ................. 239/359 |
| 3,343,797 A | * | 9/1967 | Bach ....................... 239/355 |
| 3,354,883 A | * | 11/1967 | Southerland ............... 222/82 |
| 3,369,757 A | * | 2/1968 | Boris ...................... 239/355 |
| 3,425,598 A | * | 2/1969 | Kobernick ................. 222/82 |
| 3,613,680 A | * | 10/1971 | Zamarra ................... 222/92 |
| 3,655,096 A | * | 4/1972 | Easter ..................... 222/82 |
| 3,730,392 A | * | 5/1973 | Marand .................... 222/82 |
| 3,790,034 A | * | 2/1974 | Horvath .................. 222/153 |
| 3,897,006 A | * | 7/1975 | Tada ...................... 239/333 |
| 3,927,834 A | * | 12/1975 | Tada ...................... 239/359 |
| 3,933,279 A | * | 1/1976 | Maier ..................... 222/193 |
| 4,061,698 A | * | 12/1977 | Thornwald ................. 261/78 |
| 4,100,235 A | * | 7/1978 | Thornwald ................ 261/142 |
| 4,259,184 A | * | 3/1981 | D'Arnal .................... 210/85 |
| 4,440,317 A | * | 4/1984 | Clark et al. ............... 222/103 |
| 4,576,157 A | * | 3/1986 | Raghuprasad ........... 128/200.23 |
| 4,638,927 A | * | 1/1987 | Morane .................... 222/83 |
| 4,801,093 A | * | 1/1989 | Brunet et al. .............. 239/490 |

(List continued on next page.)

FOREIGN PATENT DOCUMENTS

| | | | |
|---|---|---|---|
| DE | 44 03 755 A1 | 11/1994 | |
| EP | 0 562 943 A1 | 9/1993 | |
| EP | 0562943 A1 * | 9/1993 | ............ 222/189.11 |
| WO | WO 92/04004 * | 3/1992 | ............ 222/189.11 |
| WO | WO 96/03344 A1 | 2/1996 | |
| WO | WO 97/18902 * | 5/1997 | ................. 424/45 |
| WO | WO 97/29799 | 8/1997 | |

OTHER PUBLICATIONS

A copy of the International Search Report dated Feb. 25, 2000.

*Primary Examiner*—Aaron J. Lewis
*Assistant Examiner*—Joseph F. Weiss, Jr.
(74) *Attorney, Agent, or Firm*—Finnegan, Henderson, Farabow, Garrett & Dunner, L.L.P.

(57) ABSTRACT

In existing vaporizers the medication passes through unsterilized passages which preclude heir use to administer sterile medications. The present invention therefore provides a device for dispensing a vaporized spray of sterile medicated liquid. It uses a combination atomizing and pressure release valve in which there is a flexible membrane with an aperture, and a plug extending upwardly through the aperture and having a surface against which the membrane is biassed in the closed position, the membrane lifting off the surface of the plug in the open position to thereby open the aperture.

22 Claims, 5 Drawing Sheets

U.S. PATENT DOCUMENTS

| | | | | |
|---|---|---|---|---|
| 4,955,371 A | * | 9/1990 | Zamba et al. | 128/200.18 |
| 5,064,122 A | * | 11/1991 | Kamishita et al. | 239/396 |
| 5,067,655 A | * | 11/1991 | Farago et al. | 239/124 |
| 5,147,311 A | * | 9/1992 | Pickhard | 604/153 |
| 5,224,471 A | * | 7/1993 | Marelli et al. | 128/200.14 |
| 5,232,687 A | * | 8/1993 | Geimer | 424/45 |
| 5,310,085 A | * | 5/1994 | Lontrade et al. | 222/1 |
| 5,373,971 A | * | 12/1994 | Laffy et al. | 222/189 |
| 5,373,972 A | * | 12/1994 | Bystrom et al. | 222/212 |
| 5,402,943 A | * | 4/1995 | King et al. | 239/11 |
| 5,405,084 A | * | 4/1995 | Weston et al. | 239/11 |
| 5,492,252 A | * | 2/1996 | Gueret | 222/207 |
| 5,497,944 A | * | 3/1996 | Weston et al. | 239/321 |
| 5,507,417 A | * | 4/1996 | Webb | 222/189.11 |
| 5,614,172 A | * | 3/1997 | Geimer | 424/45 |
| 5,620,434 A | | 4/1997 | Brony | |
| 5,662,271 A | * | 9/1997 | WEston et al. | 239/321 |
| 5,709,202 A | * | 1/1998 | Lloyd et al. | 128/200.14 |
| 6,019,899 A | * | 2/2000 | Webb | 210/321.75 |
| 6,053,368 A | * | 4/2000 | Geimer | 222/189.09 |
| 6,062,430 A | | 5/2000 | Fuchs | |
| 6,092,695 A | * | 7/2000 | Loeffler | 222/207 |
| 6,207,052 B1 | * | 3/2001 | Webb | 210/321.75 |
| 6,257,231 B1 | * | 7/2001 | Shick et al. | 128/200.14 |
| 6,302,101 B1 | * | 10/2001 | Py | 128/200.22 |

\* cited by examiner

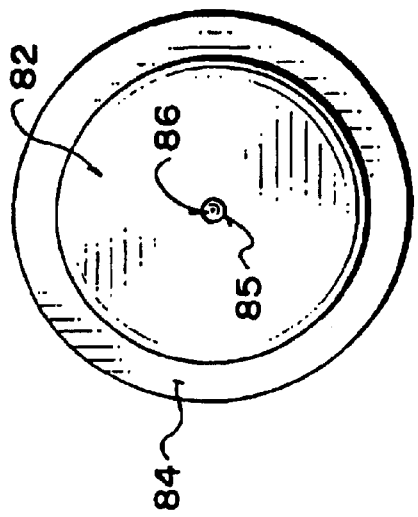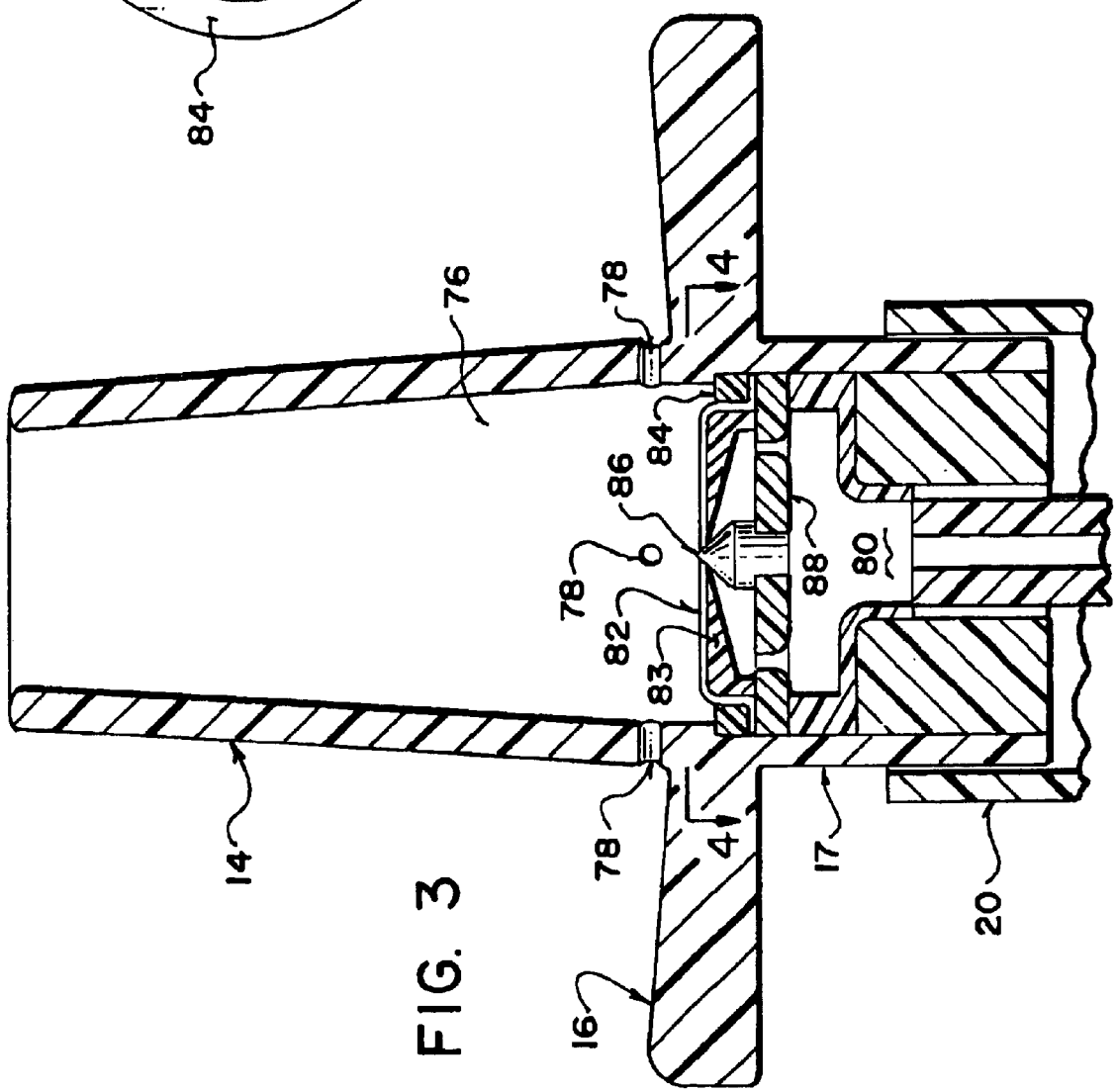

VAPORIZING DEVICE FOR ADMINISTERING STERILE MEDICATION

This application claims priority from Provisional Application Serial No. 60/105,725, filed on Oct. 27, 1998, which is incorporated by reference and relied on herein.

TECHNICAL FIELD

The invention relates to the field of devices for administering medicated liquids, and more particularly to vaporizers.

BACKGROUND ART

It is common to us vaporizers or atomizers for delivering certain medicines to humans, such as asthma medication. Many medications can be effectively delivered into the bloodstream by inhalation through the lungs. However, many medications, such as insulin, must be delivered in sterile form, which precludes the use of existing vaporizers, in which the medication passes through unsterilized passages, including the vaporizer itself. There is therefore a need for a vaporizer which can administer sterile medications.

DISCLOSURE OF INVENTION

The invention therefore provides a device for dispensing a vaporized spray of sterile medicated liquid, comprising a housing for containing a supply of sterile medicated liquid, means for pressurizing the liquid, and a combination atomizing and pressure release valve.

The invention also provides a combination atomizing and pressure release valve comprising a layer of flexible material provided with an aperture, and a plug extending through the aperture and having a surface against which the layer of flexible material is biased in the closed position, the layer lifting off the surface of the plug in the open position to thereby open the aperture.

BRIEF DESCRIPTION OF DRAWINGS

In drawings which illustrate a preferred embodiment of the invention:

FIG. 3 is a detail of the atomizer portion of the invention;

FIG. 4 is a top view taken along lines 4—4 of FIG. 3;

BEST MODE(S) FOR CARRYING OUT THE INVENTION

Figure 1:
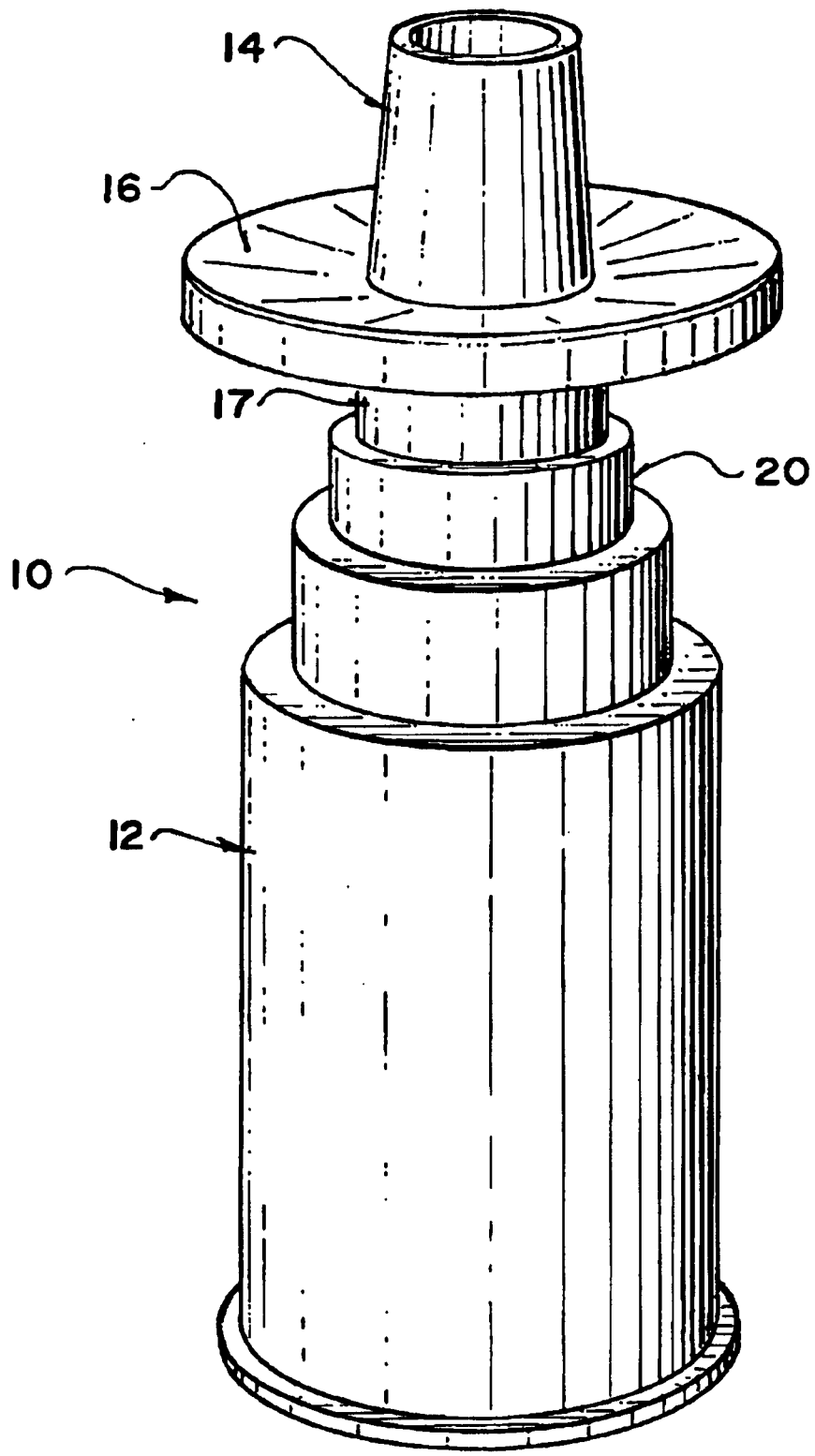
FIG. 1 is a perspective view of the invention.

The vaporizer 10 of the invention has a hollow body or housing 12, such as of molded plastic, and a tubular mouthpiece 14 connected to a circular disc 16 which receives the user's lips. The lower end of mouthpiece 14 forms a cylindrical piston 17 which slides in chamber 18 formed by cylindrical walls 20. A slight gap between piston 17 and the inner surface of walls 20 permits the passage of air. Extending downwardly and co-axially from piston 17 is an inner piston 22 which sealingly slides within chamber 24 formed by walls 26. The lower end of piston 22 is sealed at 28. Piston 22 has a central hollow tube 30 which bears against spring 32 within cylindrical chamber 36. Spring 32 in turn bears against ball valve 34 seated in opening 40 which communicates with passage 42 extending downwardly through inlet tube 38 which in turn communicates with the hollow interior 44 of housing 12.

A flexible, expandable bag 50 is sealingly secured at 52 to tube 38 and at 54 to walls 26. Air passage 56 permits air to pass from chamber 18 into the interior of flexible bag 50, which therefore expands as the liquid in chamber 44 is dish A soluble medication tablet or powder 60 is provided in the lower end of housing 12. A layer of breakable aluminum foil 62 or similar material is provided across circular opening 64 at the lower end of housing 12. A cylindrical piston 66 slides with a friction fit within chamber 68 formed by circular wall 70. The upper surface 72 of cylinder 66 bears against tablet 60. Rim 74 limits the upward travel of cylinder 66.

The vaporizer section of the invention is shown in detail in FIG. 3. Chamber 80 communicates with tube 30. Pressure release valve/atomizer 82 is formed of a flexible material such as rubber. It extends across chamber 80 and has a central hole 85, and is supported on the central axis of the housing by support 88. The upper end of plug 86 extends through the hole 85 in a manner that pressure is placed on pressure release valve 82 so the edges of hole 85 seal against the surface of plug 86 in the rest position, but when pressure is applied to the lower surface of valve 82, it lifts off the surface of plug 86. The surface of plug 86 and/or the lower surface of rubber valve 82 may be provided with swirl patterns 87 to facilitate vaporization. Air holes 78 are provided in mouthpiece 14 to provide air circulation to assist in vaporization.

Figure 7:
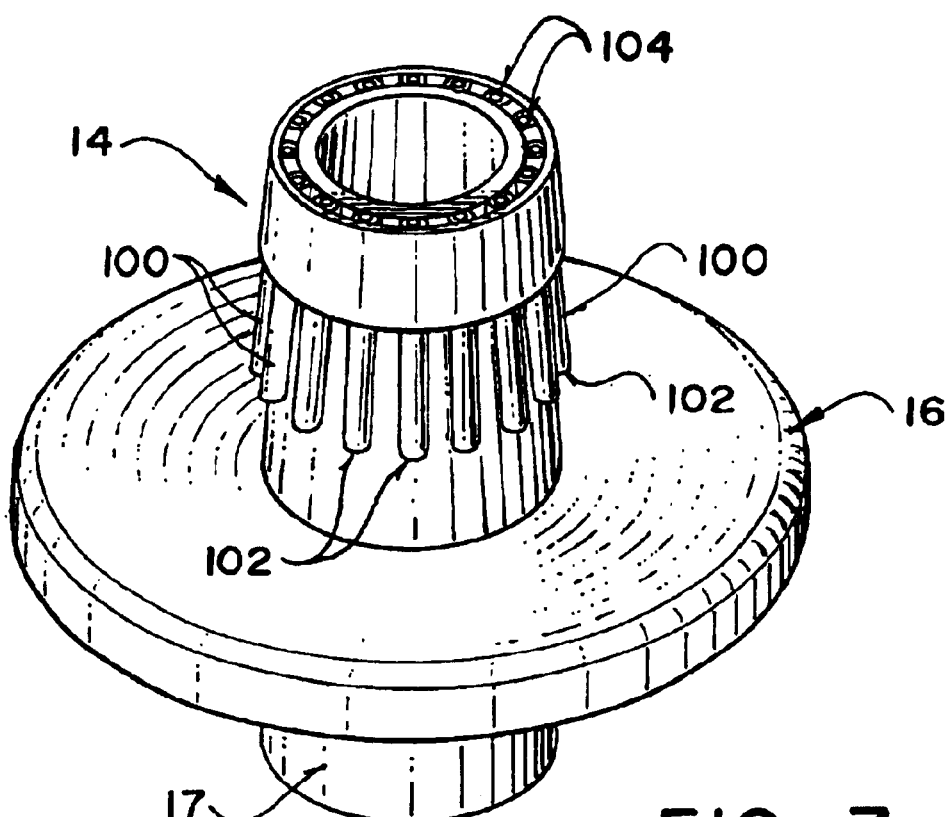
FIG. 7 is a partial elevation of the mouthpiece according to one embodiment of the invention.
Figure 8:
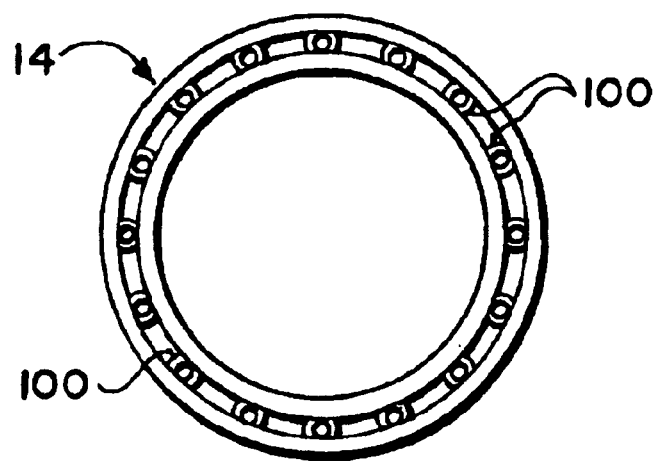
FIG. 8 is an end view of the mouthpiece shown in FIG. 8.

While plug 86 is shown as conical in shape with a pointed vertex, it could also have a blunt end, or be in the shape of a hemisphere or paraboloid, or similar smoothly curved surface. Other forms of venting of the mouthpiece to assist vaporization are also possible. For example, as shown in FIG. 7, a circular array of straw-like tubes 100 is provided extending along the outside of the mouthpiece 14 parallel to the axis of the device, open to the atmosphere at their lower ends 102. The upper ends 104 of tubes 100 open into the mouth of the user. A cylinder 106 encircles the upper portion of tubes 100 in the area where the user's lips will encircle the mouthpiece 14, and may fill in the spaces between the tubes 100. In this way passage of the vaporized medicine to user's lungs is facilitated, since the array of tubes forms a cylindrical sheath of air around the central spray of medicine. Various patterns for the tubes 100 can be provided, such as a spiral around mouthpiece 14. The upper ends 104 of tubes 100 can also be deflected to create an airfoil effect to speed the passage of the spray of medicine.

Figure 2:
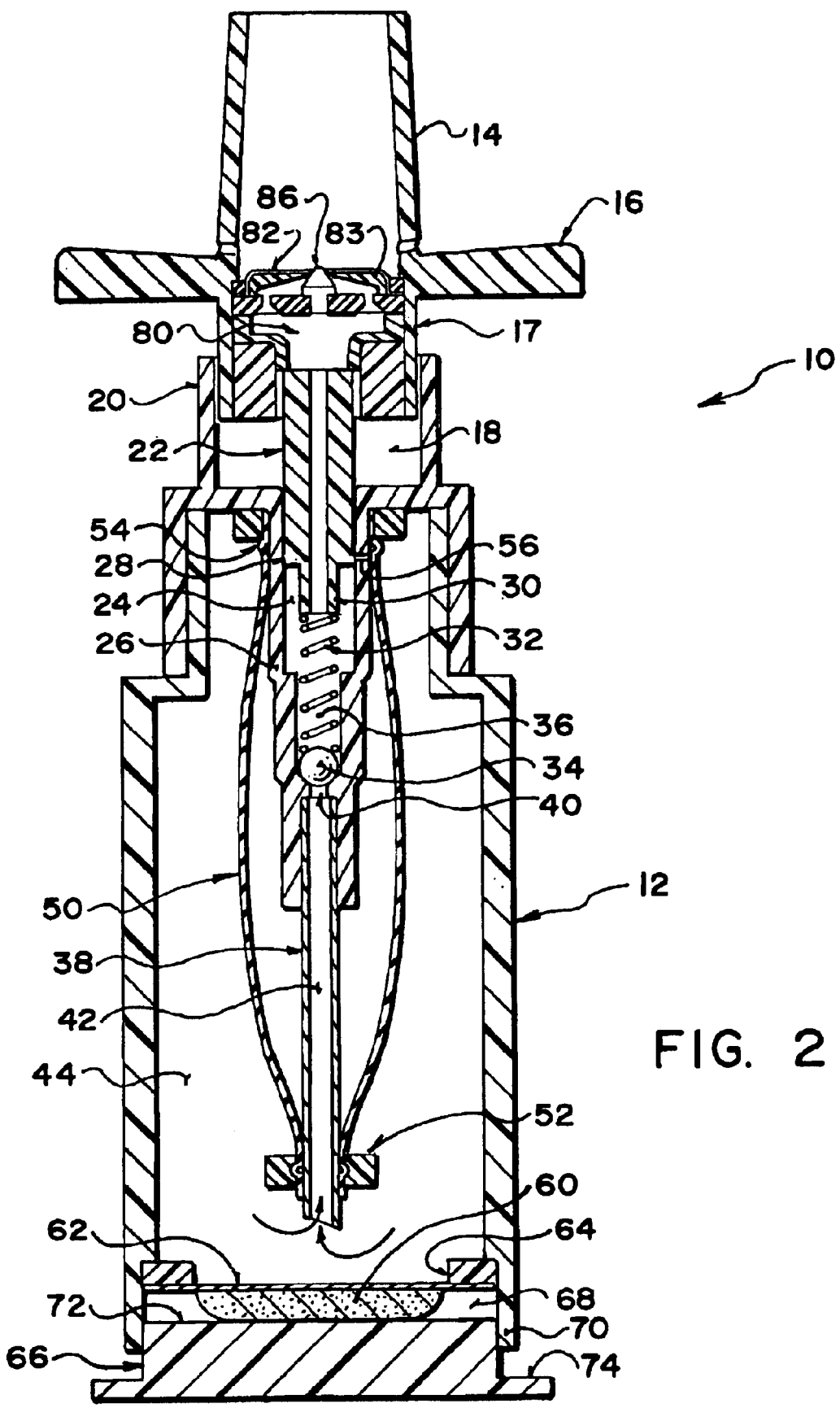
FIG. 2 is a vertical cross-section of the invention as shown in FIG. 1.
Figure 5:
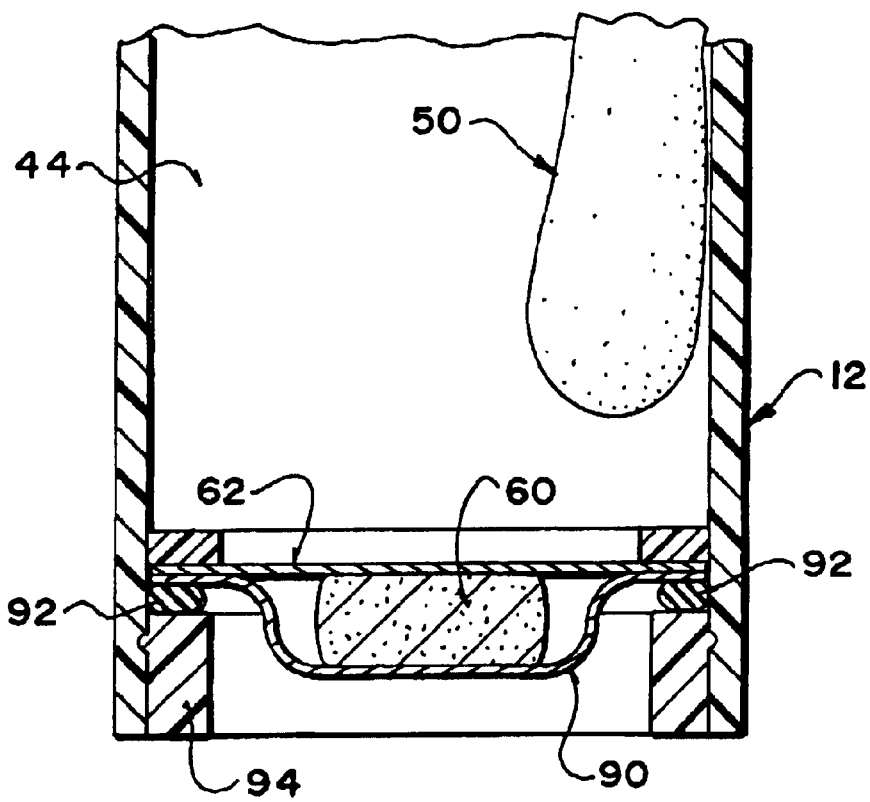
FIG. 5 is a vertical cross-section of a second embodiment of the invention.
Figure 6:
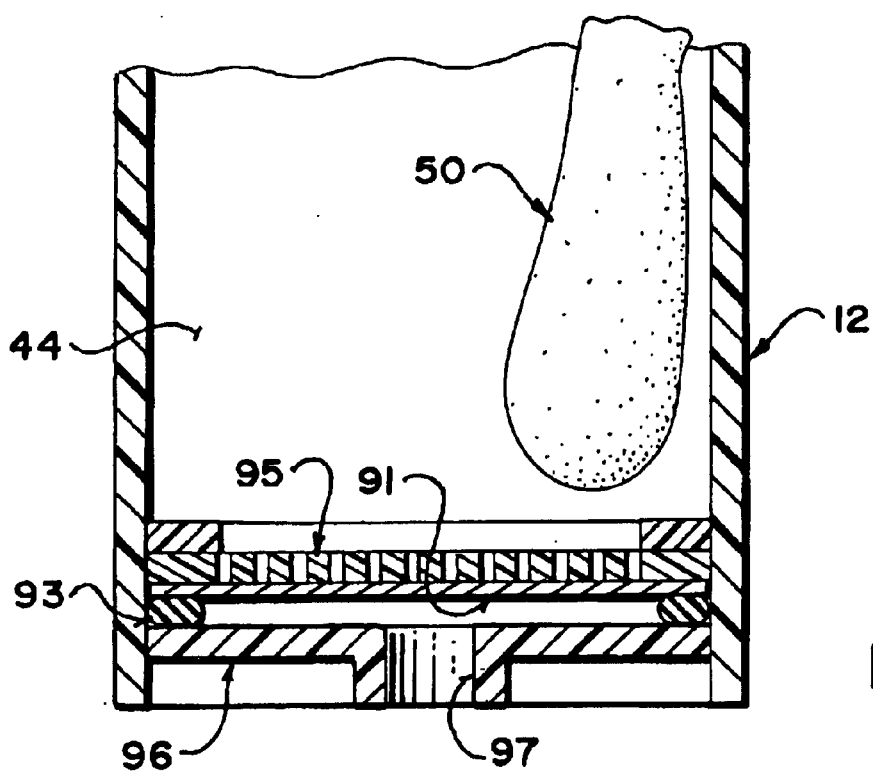
FIG. 6 is a vertical cross-section of a third embodiment of the invention.

In operation, chamber 44 is filled with a sterile liquid, such as a sterile saline solution, when the device is manufactured. The device is not designed to be refilled, and so is disposed after the liquid has been used up. When the user wishes to commence use of the device, piston 66 is pressed into the housing 12, causing tablet 60 to be forced through aluminum foil layer 62 into the sterile liquid in chamber 44, where it dissolves. The friction fit of piston 66 against walls 70 prevents leakage. To dispense the vaporized medicated liquid through mouthpiece 14, disc 16 is drawn up to the position shown in FIG. 2, which unseats ball valve 34 and draws the sterile medicated liquid up through tubes 38 and 30 into chambers 24 and 80. Disc 16 is then forced downwardly against the resistance of spring 32, causing pressure release valve 82 to lift off plug 86, allowing the liquid to spray through hole 85, and be vaporized due to the interaction of the hole 85 and plug 86. Atmospheric air is able to penetrate into chamber 18, and then through hole 56 into the interior of flexible bag 50, which expands to replace the volume of liquid which is expelled.

Preferably plug 86 is plated with silver to provide a biostatic barrier by creating silver ions which repel bacteria from entering hole 85. Similarly a small silver pellet could be added to the sterile liquid in chamber 44 to act as a mild preservative in maintaining the sterility of the liquid. While the distance between the atomic valve 82 and the pump arrangement 22/28 is shown as quite short in FIG. 2, this obviously could be made much longer by interposing a length of flexible conduit or the like.

Other constructions can be used to achieve the same effect as flexible bag 50. For example, the sterile liquid can be contained within a flexible bag within chamber 44. Tube 38 would then end within the liquid bag. There would be no air access 56 to the bag, but atmospheric air could enter around the bag in chamber 44 through an air passage in housing 12. In that event the medicine tablet 60 would be contained within the flexible liquid bag, arranged so that it could be dispensed into the liquid by pressing it through a foil seal. Another alternative to bag 50 is to load the sterile liquid in chamber 44 with a pressurized gas, as in an aerosol spray, so that depression of the mouthpiece 14/16 causes the pressurized gas and liquid to be released under pressure into chamber 80.

According to the embodiment shown in FIG. 5, the air-filled bag 50 is not secured around tube 38 but is loose within housing 12. The interior of bag 50 communicates to the atmosphere exterior to housing 12 through an opening in housing 12. In this embodiment the medicinal tablet 60 is held in place beneath foil layer 62 by a flexible membrane 90 which seals against foil layer 62 by a rubber gasket 92 held in place by retaining ring 94. Tablet 60 is introduced into the sterile liquid in chamber 44 by pressing on membrane 90, thereby forcing tablet 60 through foil layer 62.

In the embodiment shown in FIG. 6, liquid medicine is injected into the chamber 44 through a sterilizing micro-filter 91, rather than dissolving a medicated tablet in the sterile solution. Micro-filter 91 is supported between perforated filter support 95 and rubber gasket 93, which is held in place by support disc 96. Disc 96 has an attachment port into which the end of a syringe sealingly fits. To introduce the sterile medicine into the sterile solution in chamber 44, the syringe is filled with the desired amount of medicinal liquid and the end of the syringe is sealingly inserted into attachment port 97. The plunger of the syringe is depressed until the desired amount of liquid medicine is forced through micro-filter 91, at which point the syringe is removed and a plug (not shown) is then sealingly inserted into port 97.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A device for dispensing a vaporized spray of sterile medicated liquid, comprising:

a chamber arranged to contain a supply of pressurized sterile medicated liquid;

a valve arranged to move between a closed position and an open position for vaporizing the pressurized sterile medicated liquid, the valve having a support portion, a plug, and a layer of flexible material circumferentially supported by the support portion, the layer of flexible material having a first surface facing a first direction, a second surface facing a second direction different from the first direction, and an aperture;

wherein the layer of flexible material is arranged to move between a first position, where the plug is within the aperture of the layer of flexible material and the pressurized sterile medicated liquid is prevented from being dispensed from the chamber, and a second position, where the aperture of the layer of flexible material is moved away from the plug so as to simultaneously vaporize and dispense the pressurized sterile medicated liquid from the chamber;

wherein the support portion has a first thickness adjacent to a peripheral portion of the layer of flexible material and a second thickness less than the first thickness adjacent to the aperture of the layer of flexible material, and the support portion is configured to provide a gap between the support portion and the plug in the region of the aperture; and wherein the layer of flexible material is sufficiently rigid to close the gap when the pressure on the first and second surfaces is equivalent and the layer of flexible material is sufficiently flexible to cause vaporization of the pressurized sterile medical liquid when the layer of flexible material is moved away from the plug to the second position by the pressurized sterile medical liquid.

2. The valve of claim 1, wherein the aperture is centrally located in the flexible layer.

3. The valve of claim 1, wherein the plug has a smoothly curved surface.

4. The valve of claim 1, wherein the plug is conical.

5. The valve of claim 1, wherein the plug is silver plated.

6. The valve of claim 1, wherein the flexible material is rubber.

7. The device of claim 1, further comprising an expandable, flexible bag communicating with atmosphere exterior to the housing.

8. The device of claim 1, wherein the liquid is medicated by adding a soluble tablet to the liquid.

9. The device of claim 8, wherein the soluble tablet is added to the liquid by pressing the tablet through a breakable sealed barrier.

10. The device of claim 9, further comprising means for adding a sterile medication to the liquid including a soluble sterile powder configured to be added to the liquid by pressing the powder through a breakable sealed barrier in the housing.

11. The device of claim 9, further comprising means for adding a sterile medication to the liquid including a soluble sterile tablet configured to be added to the liquid by pressing the tablet through a breakable sealed barrier in the housing.

12. The device of claim 11, wherein the tablet is pressed through the sealed barrier by means of a piston slidable within the housing and arranged to bear against the tablet.

13. The device of claim 1, further comprising a mouthpiece having a central aperture communicating with the aperture of the pressure release valve.

14. The device of claim 13, wherein the means for pressurizing the liquid comprises pump means connected to the mouthpiece and reciprocable in the housing.

15. The device of claim 1, further comprising means for adding a sterile medication to the liquid comprising means for forcing a liquid medicament through a microfilter in the housing.

16. The device of claim 15, wherein the housing includes a port arranged to receive the means for adding a sterile medication to the liquid.

17. The valve of claim 1, wherein a swirl pattern is provided on the surface of the plug.

18. The device of claim 1, further comprising a housing in communication with the chamber.

19. The device of claim 18, further comprising an expandable, flexible bag in communication with atmospheric air outside of the housing.

20. The device of claim 1, further comprising a dispenser having a central aperture in communication with the aperture of the valve.

21. The device of claim 1, further comprising a pump connected to the dispenser and arranged to pressurize a supply of sterile medicated liquid in the chamber.

22. The device of claim 1, wherein the plug is arranged with silver plating to repel bacteria from entering the aperture of the layer of flexible material.

* * * * *